(12) United States Patent
Sartor

(10) Patent No.: US 11,751,866 B2
(45) Date of Patent: Sep. 12, 2023

(54) ENDOSCOPIC STITCHING DEVICE HAVING ANGLED SUTURE NEEDLE

(71) Applicant: Covidien LP, Mansfield, MA (US)

(72) Inventor: Joe D. Sartor, Longmont, CO (US)

(73) Assignee: Covidien LP, Mansfield, MA (US)

( * ) Notice: Subject to any disclaimer, the term of this patent is extended or adjusted under 35 U.S.C. 154(b) by 232 days.

(21) Appl. No.: 17/179,717

(22) Filed: Feb. 19, 2021

(65) Prior Publication Data

US 2021/0330317 A1 Oct. 28, 2021

Related U.S. Application Data

(60) Provisional application No. 63/015,043, filed on Apr. 24, 2020.

(51) Int. Cl.
*A61B 17/04* (2006.01)
*A61B 17/06* (2006.01)

(52) U.S. Cl.
CPC .... *A61B 17/0469* (2013.01); *A61B 17/06066* (2013.01); *A61B 2017/06071* (2013.01)

(58) Field of Classification Search
CPC .......... A61B 17/0469; A61B 17/00234; A61B 17/06166; A61B 17/0625; A61B 17/12013; A61B 17/0491; A61B 17/06066; A61B 2017/06071; A61B 2017/0417; A61B 2017/06047; A61B 2017/0609

See application file for complete search history.

(56) References Cited

U.S. PATENT DOCUMENTS

| 5,389,103 A * | 2/1995 | Melzer ............... A61B 17/0469 606/147 |
| 5,591,181 A * | 1/1997 | Stone ................. A61B 17/0469 606/144 |
| 5,674,230 A * | 10/1997 | Tovey ................ A61B 17/0469 606/139 |
| 5,871,488 A | 2/1999 | Tovey et al. |
| 5,908,428 A | 6/1999 | Scirica et al. |
| 5,947,982 A | 9/1999 | Duran |
| 6,051,006 A | 4/2000 | Shluzas et al. |
| 2011/0040308 A1 | 2/2011 | Cabrera et al. |

(Continued)

FOREIGN PATENT DOCUMENTS

EP 3357432 A2 8/2018

OTHER PUBLICATIONS

Extended European Search Report issued in European Patent Application No. 21170136.2, dated Jul. 16, 2021.

*Primary Examiner* — Tuan V Nguyen

(74) *Attorney, Agent, or Firm* — Carter, DeLuca & Farrell LLP

(57) ABSTRACT

A surgical stitching device includes a suture needle configured to reliably pass through a typically thick scarred tissue present along, e.g., an edge of midline hernias. The surgical stitching device includes first and second jaws. The suture needle is selectively supported on the first or second jaws at, e.g., an acute, angle with respect to a longitudinal axis defined by the corresponding first or second jaw. The suture needle may be selectively secured with the first or second jaw by first and second needle receiving blades configured for reciprocating axial displacement. A suture is connected to the suture needle to perform suturing of tissue.

20 Claims, 11 Drawing Sheets

(56) References Cited

U.S. PATENT DOCUMENTS

2012/0150197 A1\* 6/2012 Malkowski ........ A61B 17/0625
606/144
2017/0071597 A1\* 3/2017 Gorski ............. A61B 17/06166
2017/0340320 A1 11/2017 Baril \* cited by examiner

ENDOSCOPIC STITCHING DEVICE HAVING ANGLED SUTURE NEEDLE

CROSS-REFERENCE TO RELATED APPLICATION

The present application claims the benefit of and priority to U.S. Provisional Patent Application Ser. No. 63/015,043, filed on Apr. 24, 2020, the entire content of which is incorporated herein by reference.

TECHNICAL FIELD

The disclosure relates to surgical devices for suturing or stitching and, more particularly, to an endoscopic suturing or stitching device including a tool assembly supporting a suture needle at an acute angle.

BACKGROUND

One of the advances in recent years to reduce the invasiveness of surgical procedures is endoscopic surgery. Generally, endoscopic surgery involves incising through body walls. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the navel incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. In such surgical procedures, it is necessary to manipulate a suture needle, having a length of suture material attached thereto, with a surgical stitching device.

SUMMARY

The disclosure describes a surgical stitching device that demonstrates a practical approach to meeting the performance requirements and overcoming usability challenges associated with suturing tissue.

In accordance with this disclosure, a surgical stitching device includes an elongate shaft assembly including an axial rod extending therethrough, and a tool assembly coupled with the elongate shaft assembly. The tool assembly includes first and second jaws, first and second needle receiving blades slidably disposed in the respective first and second jaws, and a suture needle. The first jaw is operatively coupled with the axial rod of the elongate shaft such that axial displacement of the axial rod transitions the first and second jaws between open and closed configurations. The suture needle is supported on the first or second jaws and defines an acute angle with respect to a longitudinal axis defined by the tool assembly. The suture needle is detachably secured to one of the first and second jaws by a corresponding first or second needle receiving blade.

In an aspect, the first and second jaws may include respective first and second receiving portions configured to support the suture needle.

In another aspect, the first and second receiving portions may include opposing planar surfaces defining respective acute angles with respect to the longitudinal axis of the tool assembly.

In yet another aspect, the first receiving portion of the first jaw may be proximal of the second receiving portion of the second jaw.

In still yet another aspect, the suture needle may be a straight needle.

In an aspect, the acute angle may be about 45 degrees.

In another aspect, the first and second receiving portions may define respective bores orthogonal to the respective planar surfaces. The bores may be configured to receive a portion of the suture needle therein.

In yet another aspect, the first and second needle receiving blades may include respective notches configured to engage the suture needle.

In still yet another aspect, the suture needle may define circular grooves on opposite ends of the suture needle.

In an aspect, the suture needle may extend distally when the suture needle is supported on the first jaw.

In another aspect, the suture needle may extend proximally when the suture needle is supported on the second jaw.

In accordance with another aspect of the disclosure, a tool assembly for use with a surgical stitching device includes a suture needle having first and second ends, first and second jaws transitionable between open and closed configurations, and first and second needle receiving blades axially movable in reciprocating manner. The first jaw includes a first elongate portion and a first receiving portion configured to support the first end of the suture needle. The second jaw includes a second elongate portion longer than the first elongate portion and a second receiving portion configured to support the second end of the suture needle. The suture needle defines an acute angle with respect to a longitudinal axis defined by the tool assembly when supported on the first or second jaws. The first and second needle receiving blades engage the respective first and second ends of the suture needle to secure the suture needle to the corresponding first or second jaw.

In an aspect, the acute angle may be about 45 degrees.

In another aspect, the suture needle may be parallel to the longitudinal axis when supported on the first jaw in the open configuration.

In yet another aspect, the suture needle may define an axis.

In still yet another aspect, the second receiving portion of the second jaw may be distal of the first receiving portion of the first jaw.

In still yet another aspect, the first and second receiving portions of the first and second jaws may include respective planar surfaces and define respective bores configured to receive a portion of the suture needle. The first and second receiving portions of the first and second jaws may extend distally from the respective first and second elongate portions.

In an aspect, the first jaw may include a camming pin configured to slidably engage an arcuate camming slot defined in the second jaw.

In another aspect, the tool assembly may further include a linkage member pivotably interconnecting the first and second jaws.

In yet another aspect, the first and second jaws may define respective channels configured to slidably receive the first and second blades, and respective bores configured to support the suture needle. Each bore may be in communication with the corresponding channel.

In yet another aspect, the second jaw moves in an arc when farthest from the first jaw and as the second jaw approaches the first jaw, movement of the second jaw becomes linear translation to pass the suture needle into the angular bore of the first jaw, whereby the linear translation increases the force driving the suture needle over the driving force in the angular rotation portion of travel.

BRIEF DESCRIPTION OF DRAWINGS

The above and other aspects and features of this disclosure will become more apparent in view of the following detailed description when taken in conjunction with the accompanying drawings wherein like reference numerals identify similar or identical elements.

DETAILED DESCRIPTION

Figure 1:
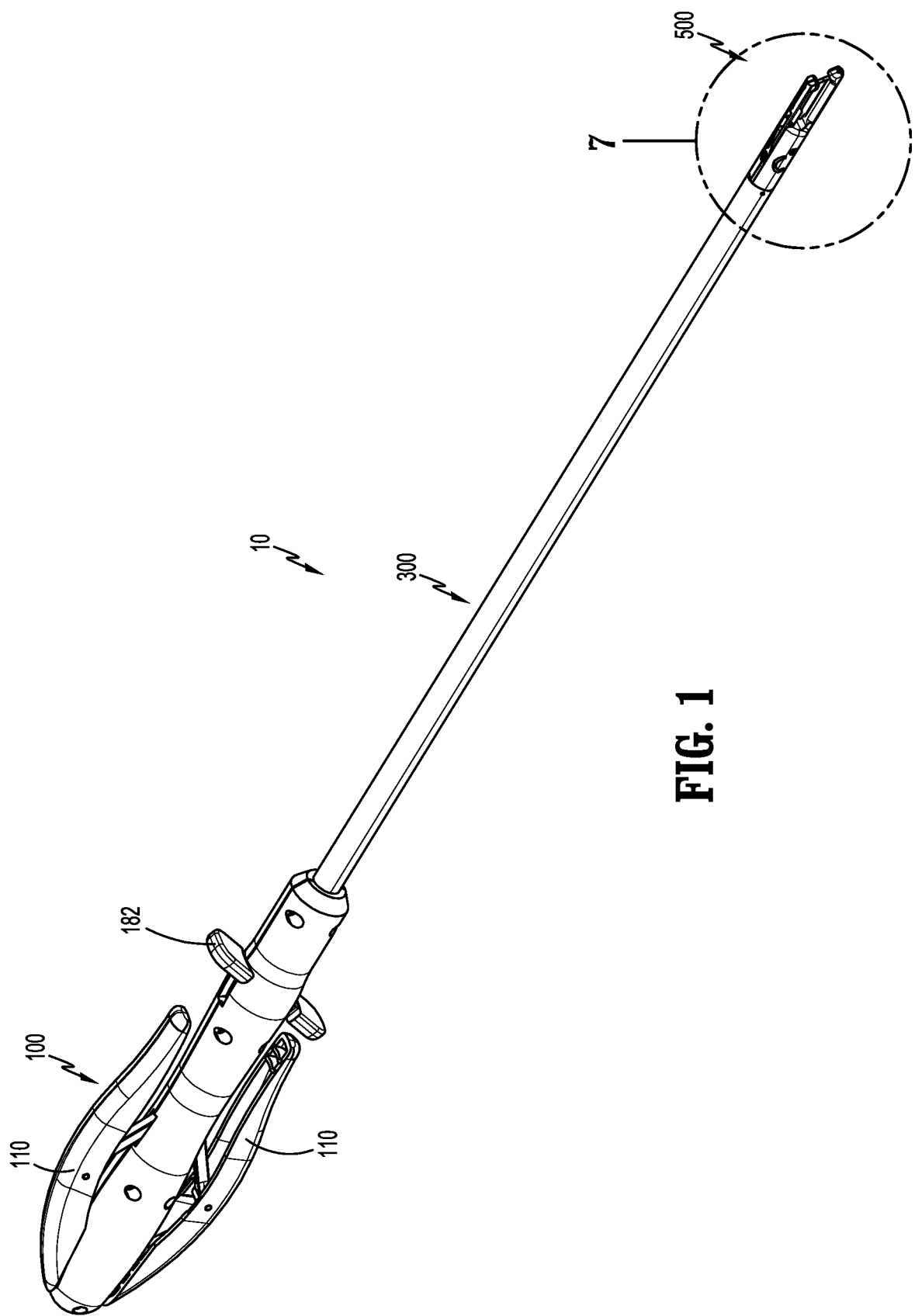
FIG. 1 is a perspective view of a surgical stitching device in accordance with the disclosure.

The surgical stitching device disclosed herein is described in detail with reference to the drawings, in which like reference numerals designate identical or corresponding elements in each of the several views.

As used herein, the term "distal" refers to the portion that is being described which is farther from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Figure 2:
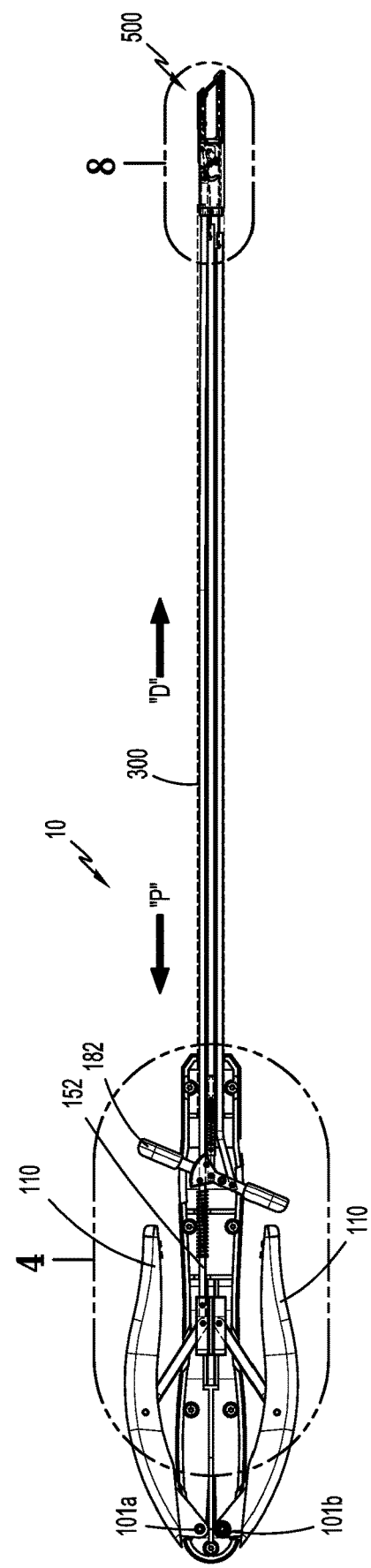
FIG. 2 is a side view of the surgical stitching device of FIG. 1 with portions of a housing and an elongate member removed.

In FIGS. 1 and 2, an exemplary surgical stitching device in accordance with the disclosure is shown generally as 10. The surgical stitching device 10 is adapted to be particularly useful in endoscopic or laparoscopic procedures. For example, the surgical stitching device 10 may be utilized in ventral hernia procedures. An endoscopic portion of the surgical stitching device 10 such as, e.g., a tool assembly 500, is insertable into an operative site, via a cannula assembly or the like (not shown). The surgical stitching device 10 includes a suture needle 199 (FIG. 3) that is supported at, e.g., an acute, angle, with respect first or second jaws 504, 506 (FIG. 3) of the tool assembly 500. Positioning the suture needle 199 at an angle within the tool assembly 500 allows a longer suture needle to be used compared to a tool assembly where the suture needle is orthogonal to the tool assembly, which, in turn, facilitates passage of the suture needle 199 through a typically thick scarred tissue present, e.g., along an edge of midline hernias. The surgical stitching device 10 includes a handle assembly 100, an elongate shaft assembly 300 extending distally from handle assembly 100, and a tool assembly 500 supported on a distal end of elongate shaft assembly 300.

Figure 3:
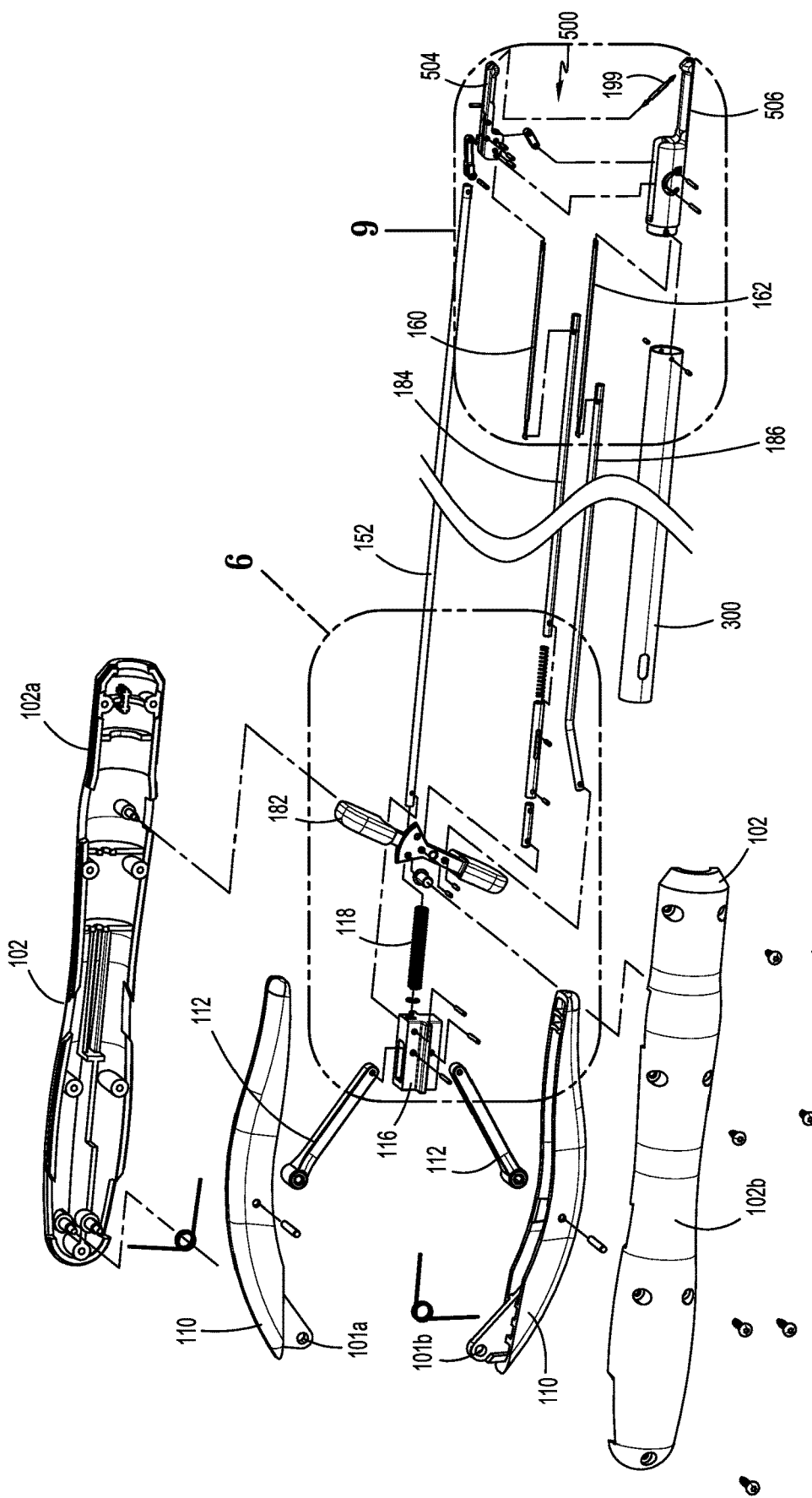
FIG. 3 is a partial exploded perspective view, with parts separated, of the surgical stitching device of FIG. 1.
Figure 4:
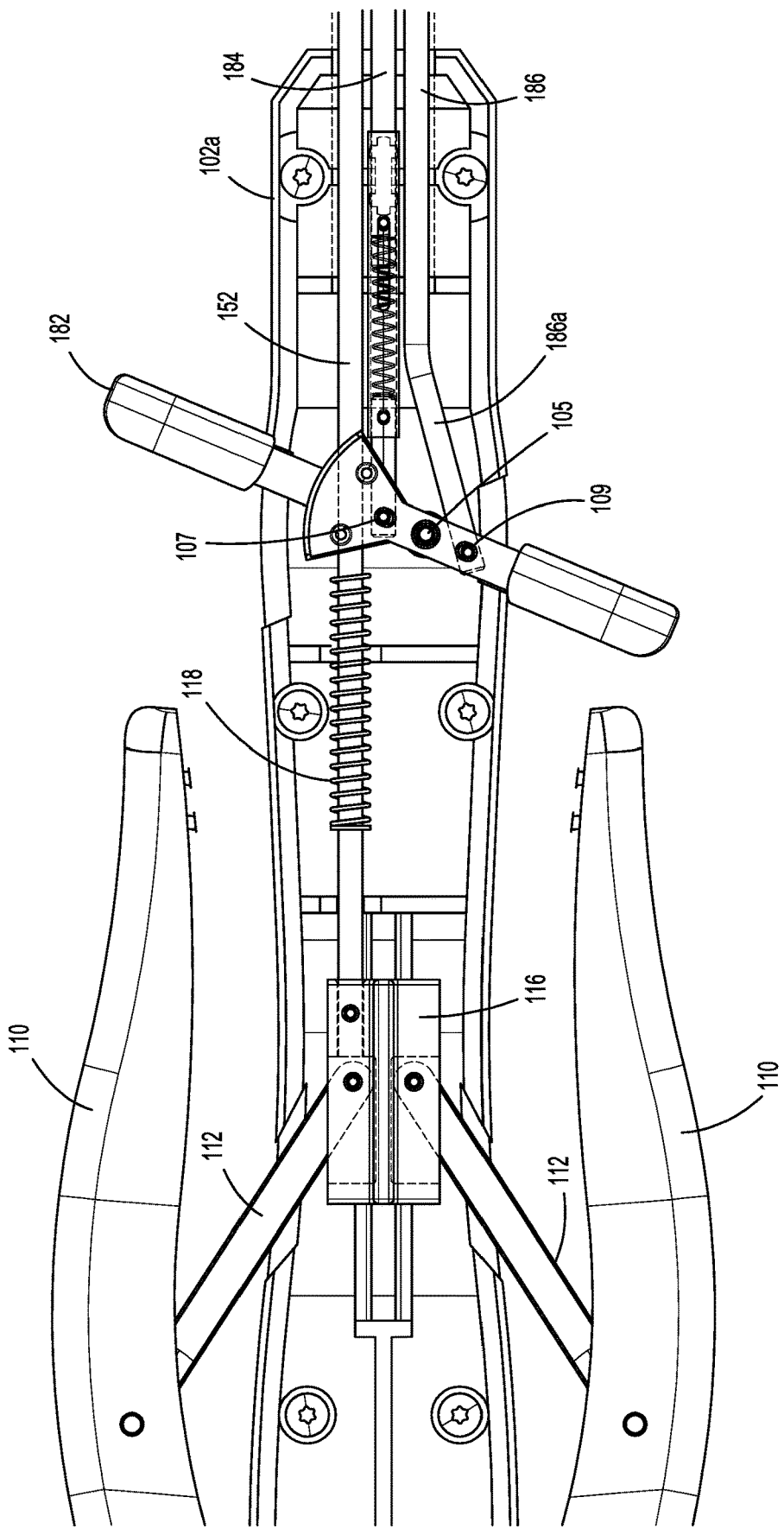
FIG. 4 is an enlarged side view of the indicated area of detail of FIG. 2.

FIGS. 3 and 4 illustrate the handle assembly 100 including a housing 102 having first and second housing halves 102a, 102b, a pair of handles 110 pivotably secured to the housing 102 about respective pivots 101a, 101b, a lever 182 pivotably supported in the housing 102 and extending transversely from the housing 102, and a coupling portion 116. The pair of handles 110 is operatively coupled to an axial rod 152 such that when the pair of handles 110 is squeezed, the axial rod 152 is displaced distally. The axial rod 152 is operatively coupled with the tool assembly 500 to transition the tool assembly 500 between open and closed configurations, as will be discussed hereinafter. The pair of handles 110 is pivotably secured to the housing 102 about the respective pivots 101a, 101b. Further, the pair of handles 110 is pivotably coupled to linkages 112 that are pivotably coupled to the coupling portion 116. The coupling portion 116 is coupled to the axial rod 152 to impart concomitant axial displacement to the axial rod 152. In particular, the axial rod 152 is biased proximally in the direction of an arrow "P" (FIG. 2) by a spring 118. Under such a configuration, the proximally biased axial rod 152 positions the coupling portion 116 in a proximal position, which, in turn, places the pair of handles 110 in a spaced apart (i.e., unactuated) configuration. When the pair of handles 110 is squeezed by the clinician, the coupling portion 116 is displaced distally in the direction of an arrow "D" (FIG. 2), which imparts axial displacement to the axial rod 152 in the same direction. The axial rod 152 is operatively coupled to the tool assembly 500 such that axial displacement of the axial rod 152 transitions a first jaw 504 towards or away from a second jaw 506 between the open and closed positions, as will be discussed hereinafter.

Figure 5:
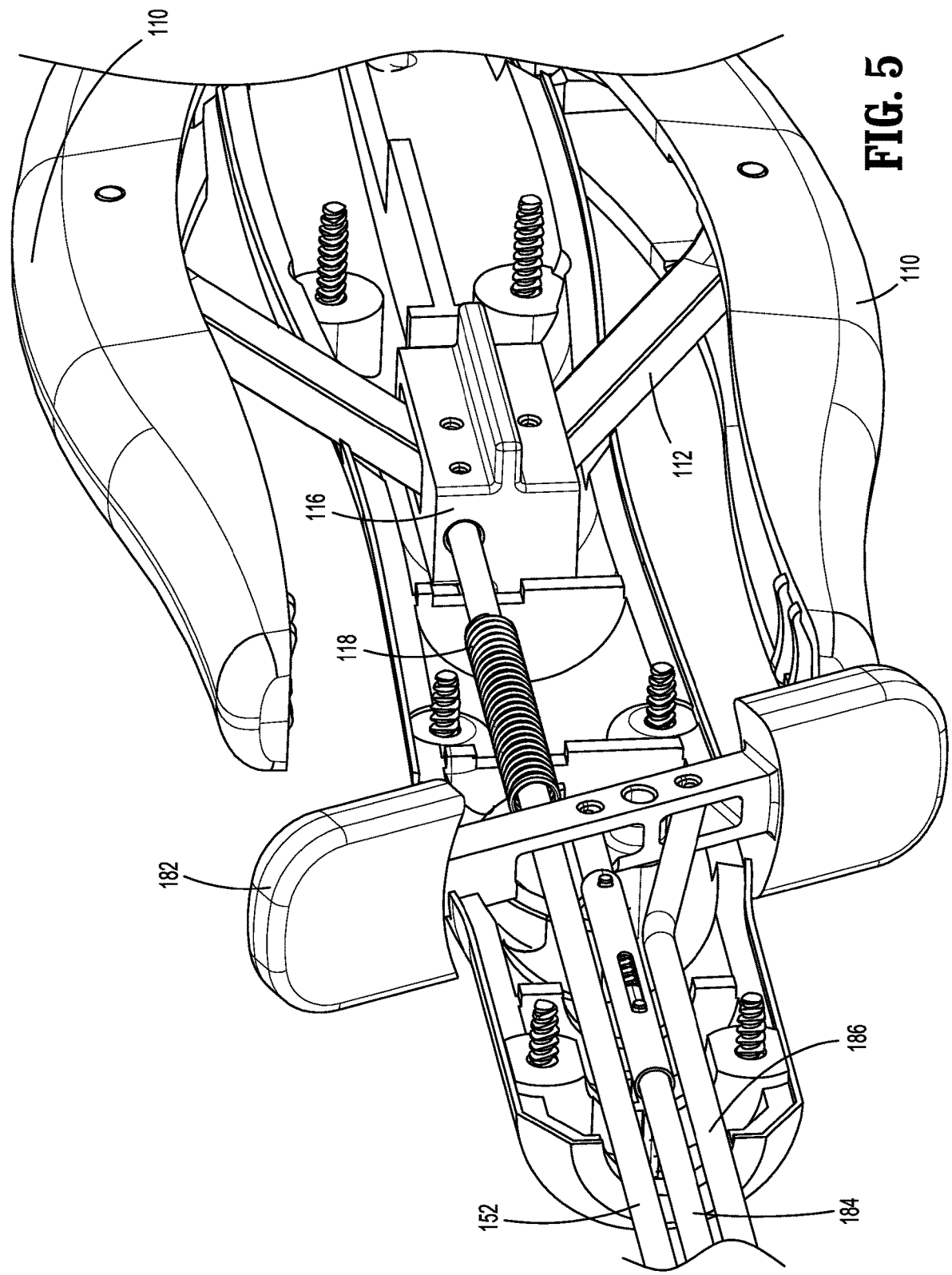
FIG. 5 is a partial perspective view of a handle assembly of the surgical stitching device of FIG. 1 with a housing half removed.
Figure 6:
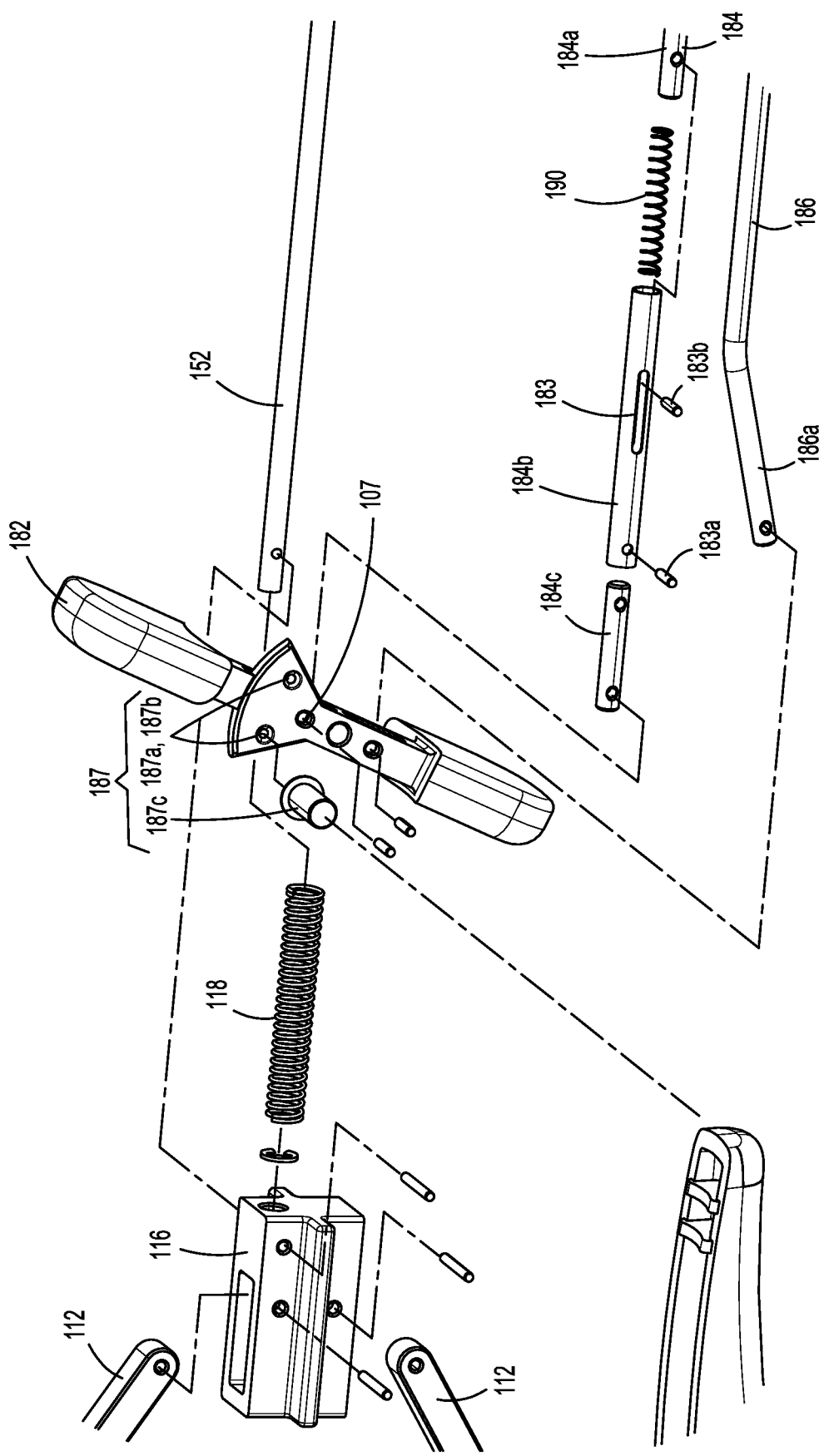
FIG. 6 is a partial exploded perspective view, with parts separated, of the indicated area of detail of FIG. 3.

FIGS. 4-6 illustrate the lever 182 pivotably coupled to the housing 102 about the pivot 105. The lever 182 is operatively coupled to first and second blades 160, 162 (FIG. 3) via the first and second drive shafts 184, 186. The first and second blades 160, 162 are configured to selectively engage the suture needle 199 (FIG. 11), thereby enabling swapping of the suture needle 199 between the first and second jaws 504, 506. In particular, the first and second drive shafts 184, 186 are pivotably coupled to the lever 182 about respective pivots 107, 109. The pivots 107, 109 are laterally spaced apart on opposing sides of the lever 182 about the pivot 105. In particular, the first and second drive shafts 184, 186 are slidably supported along the length of the elongate shaft assembly 300 such that axial displacement of the first and second drive shafts 184, 186 are imparted to the respective first and second blades 160, 162, as will be described hereinafter. The first drive shaft 184 may be, e.g., substantially parallel, to the axial rod 152. The first drive shaft 184 includes a body portion 184a, an adapter portion 184b, and a linkage 184c. The linkage 184c is pivotably coupled to the lever 182 about the pivot 107. The linkage 184c is also coupled to the adapter portion 184b by a pin 183a. The body portion 184a cammingly engages the adapter portion 184b by a camming pin 183b coupled to the body portion 184a. The camming pin 183b rides in a slot 183 defined in the adapter portion 184b. Further, the adapter portion 184b may include a spring 190 to bias the body portion 184a away from the linkage 184c, e.g., in a distal direction. The lever 182 may include a detent mechanism 187 to maintain the relative position of the first and second drive shafts 184, 186. In particular, the detent mechanism 187 includes recesses 187a, 187b defined in the lever 182 and a boss 187c extending from the housing 102 and configured to frictionally engage the recesses 187a, 187b. Under such a configuration, the detent mechanism 187 may maintain the first drive shaft 184 in a proximal-most position, while the second drive shaft 186 is in a distal-most position such that the second blade 162 is positioned to engage the suture needle 199. Similarly, the detent mechanism 187 may maintain the first drive shaft 184 in a distal-most position, while the second drive shaft 186 is in a proximal-most position such that the first blade 160 is positioned to engage the suture needle 199. The second drive shaft 186 includes a portion 186a that defines, e.g., an acute, angle with respect to the longitudinal axis "L-L" such that pivoting of the lever 182 causes reciprocating axial displacement of the first and second blades 160, 162 to enable swapping of the suture needle 199 between the first and second jaws 504, 506.

Figure 7:
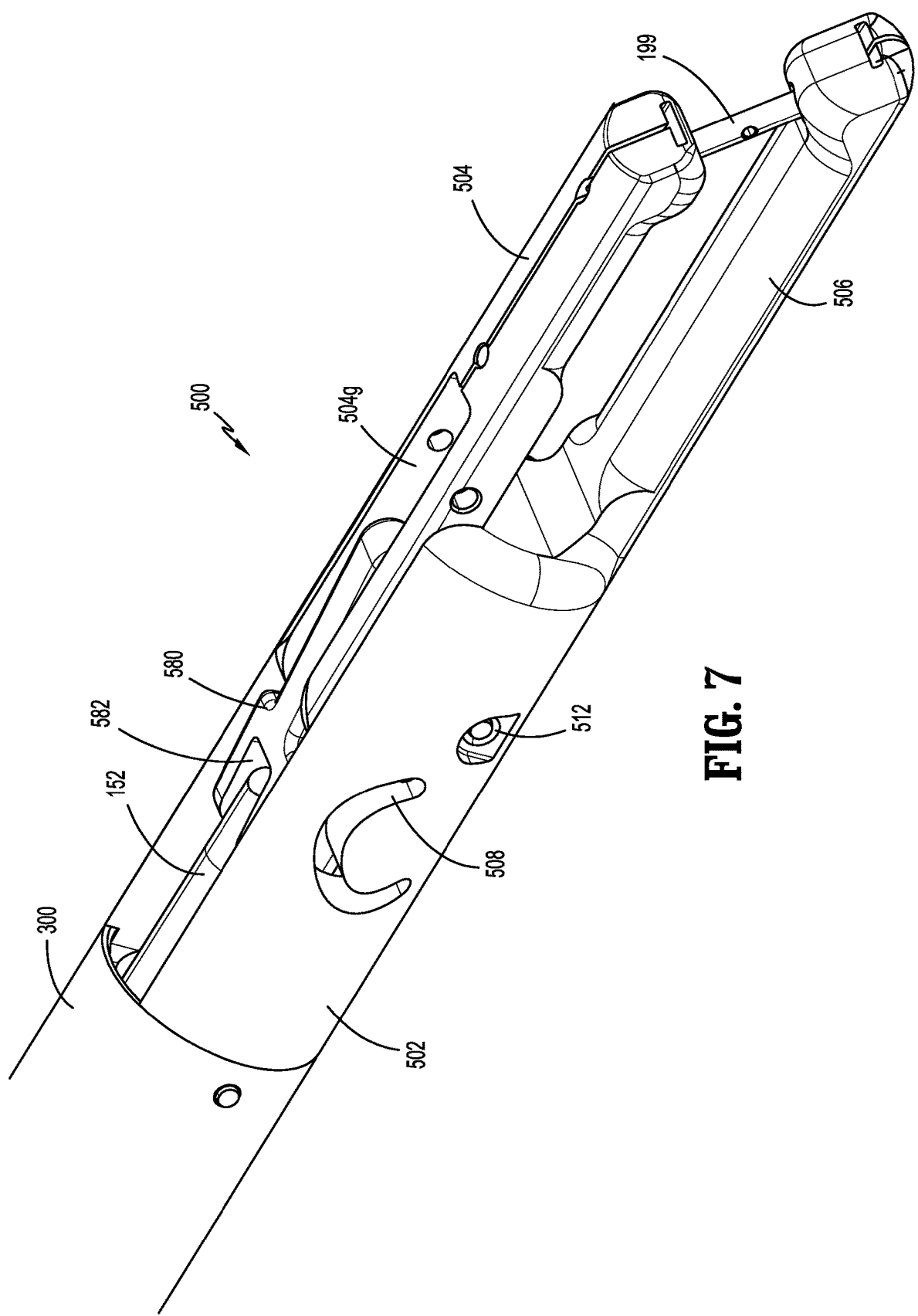
FIG. 7 is an enlarged perspective view of the indicated area of detail of FIG. 1.
Figure 8:
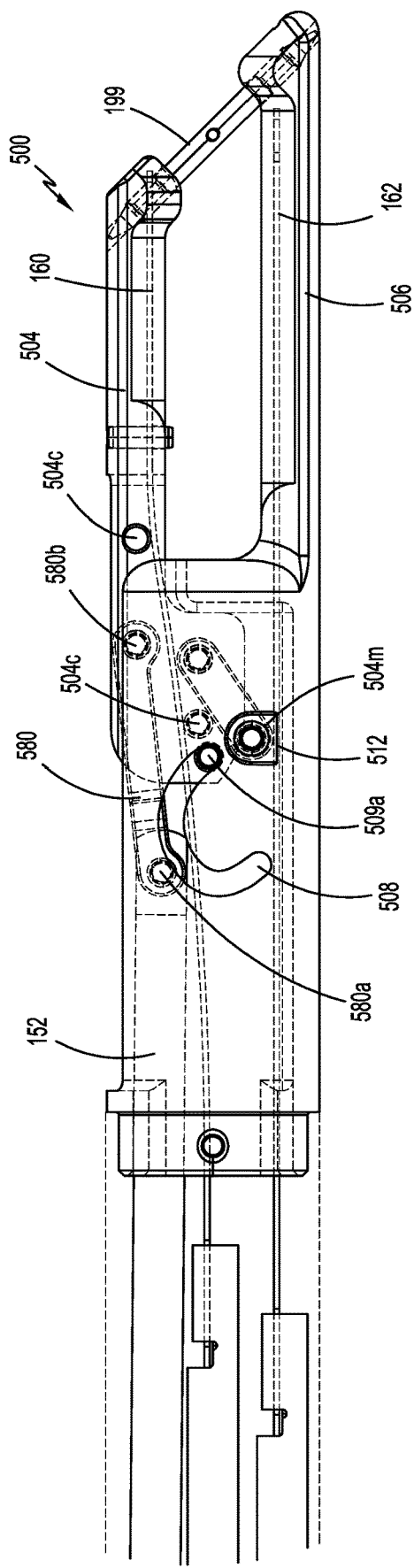
FIG. 8 is a side view of the indicated area of detail of FIG. 2.

FIGS. 7 and 8 illustrate the tool assembly 500 coupled to a distal end portion of the elongate shaft assembly 300. The tool assembly 500 includes a supporting portion 502 coupled to the elongate shaft assembly 300, a first jaw 504 movably coupled to the supporting portion 502, and a second jaw 506 fixedly coupled to the supporting portion 502. In particular, the first jaw 504 is movable between the closed configuration, in which, the suture needle 199 engages both the first and second jaws 504, 506, and the open configuration, in which, the suture needle 199 is supported on one of the first and second jaws 504, 506 and spaced apart from the other one of the first and second jaws 504, 506. The first jaw 504 is coupled to the axial rod 152. In particular, the axial rod 152 is pivotably coupled to a linkage member 580 about a pivot 580a. The linkage member 580 defines a slot 582 configured to pivotably receive a distal end of the axial road 152 therein. The linkage member 580 is pivotably coupled to the first jaw 504 about a pivot 580b. In particular, the first jaw 504 defines a slot 504j configured to pivotably receive a portion of the linkage member 580 therein.

Figure 9:
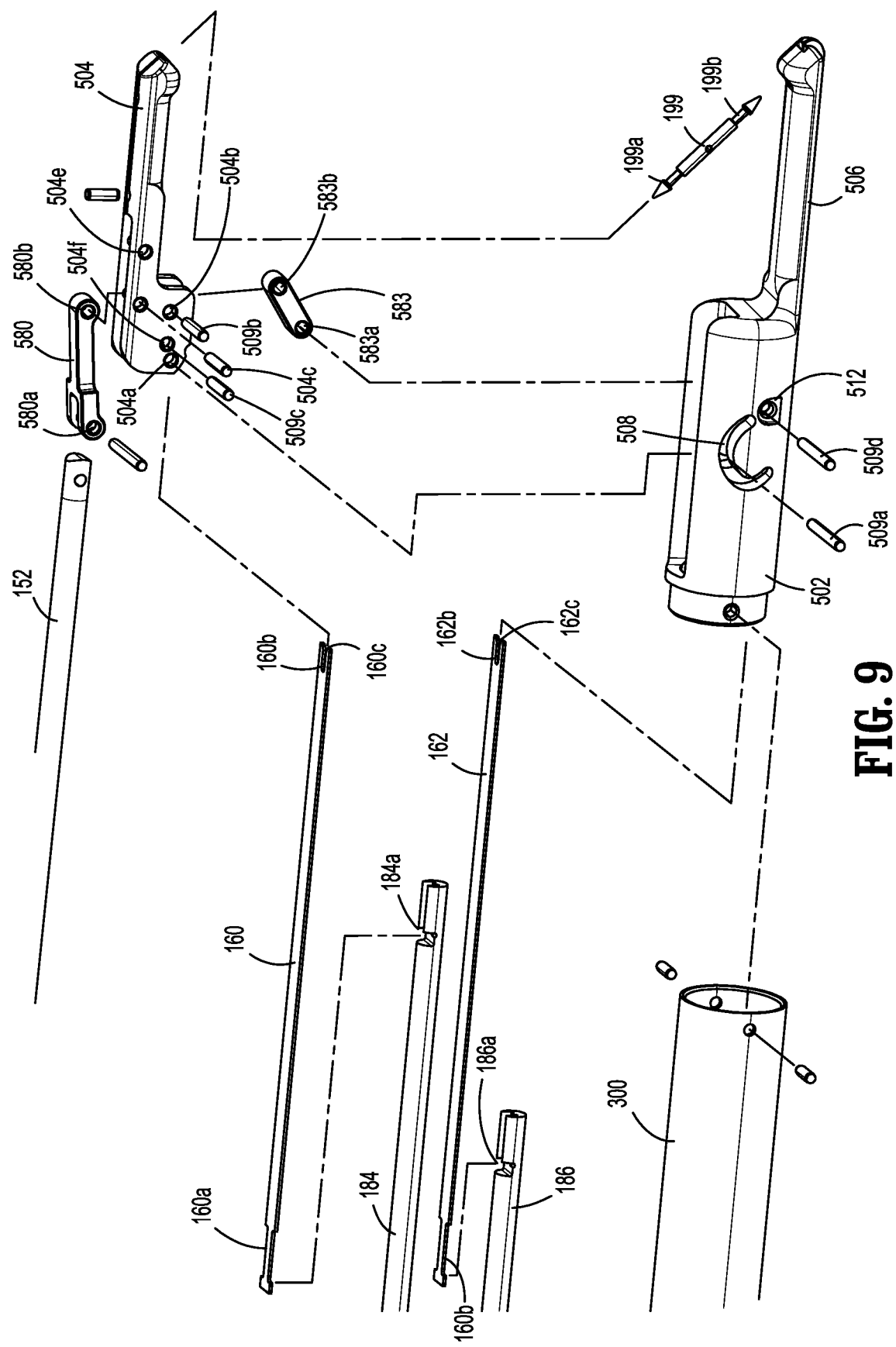
FIG. 9 is an enlarged view of the indicated area of detail of FIG. 3.

FIG. 9 illustrates the supporting portion 502 of the tool assembly 500 defining a slot 508 and a bore 512. In particular, the slot 508 has an arcuate profile, and the bore 512 is defined distal of the slot 508. The first jaw 504 includes a camming pin 509a secured to a bore 504a and cammingly engaging the slot 508, and a pivot pin 509b received in a bore 504b and pivotably securing a second linkage member 583 about a pivot 583b. The second linkage member 583 is pivotably coupled to the supporting portion 502 about a pivot 583a by a pin 509d received in a bore 512 defined in the supporting portion 502. The first jaw 504 further defines bores 504f, 504e configured to receive pins 504c (only one shown) to guide the first blade 160.

FIG. 9 illustrates the orientation of first jaw 504 at the end of the linear portion of the stroke. The linkage member 580 is in direct opposition between the axial rod 152 and the root of first jaw 504 such that the force applied to the axial rod 152 translates to a closure force having lever loss only as multiple of the COS of the angle formed between the suture needle 199 and the longitudinal axis of the instrument. This provides extensive advantage over the prior art where the force loss is typical lever ratio, i.e., the ratio of pivot to jaw end or suture needle location and the pivot to actuator which can be on the order of 5:1.

The first and second blades 160, 162 include respective proximal end portions 160a, 162a that are configured to engage respective distal end portions 184a, 186a of the first and second drive shafts 184, 186. The distal portions 184a, 186a define grooves having a shape complementary to a shape of the proximal end portions 160a, 162a. In this manner, the first and second blades 160, 162 are movable with the respective first and second drive shafts 184, 186 as a single construct. The respective first and second blades 160, 162 define respective notches 160c, 162c at distal end portions 160b, 162b. The distal end portions 160b, 162b of the first and second blades 160, 162 slidably extend into blade receiving channels (not shown) of the respective first and second jaws 504, 506. By advancing the first or second blade 160, 162 within the respective blade receiving channel, the notch 160c, 162c defined in the distal end portion 160b, 162a of advancing first or second blade 160, 162 engages or "locks in" the groove 199a, 199b of the suture needle 199 to support the suture needle 199 on the corresponding first or second jaw 504, 506. A suture (not shown) is connected to the suture needle 199. The suture may include a plurality of barbs oriented to resist movement in a direction opposite to the direction of insertion.

Under such a configuration, the lever 182 may be pivoted between a first position, in which, the first blade 160 is in a distal-most position to secure the suture needle 199 with the first jaw 504. At this time, the second blade 162 is in a proximal-most position and disengaged from the second jaw 506. As the lever 182 is pivoted to a second position, the second blade 162 is in a distal-most position to secure the suture needle 199 with the second jaw 506. At this time, the first blade 160 is in a proximal-most position. In this manner, engagement of the suture needle 199 is swapped from one of the first or second blades 160, 162 to the other one of the first or second blades 160, 162.

One can appreciate that as the first jaw 504 opens, its relative position to the shaft of the instrument moves proximal and as it closes moves back to the original distal location. The spring 190 enclosed within the adapter portion 184b is positioned on the first drive shaft 184 to facilitate the proximal to distal movement without movement of the lever 182 nor the loss of engagement with the suture needle 199.

Figure 10:
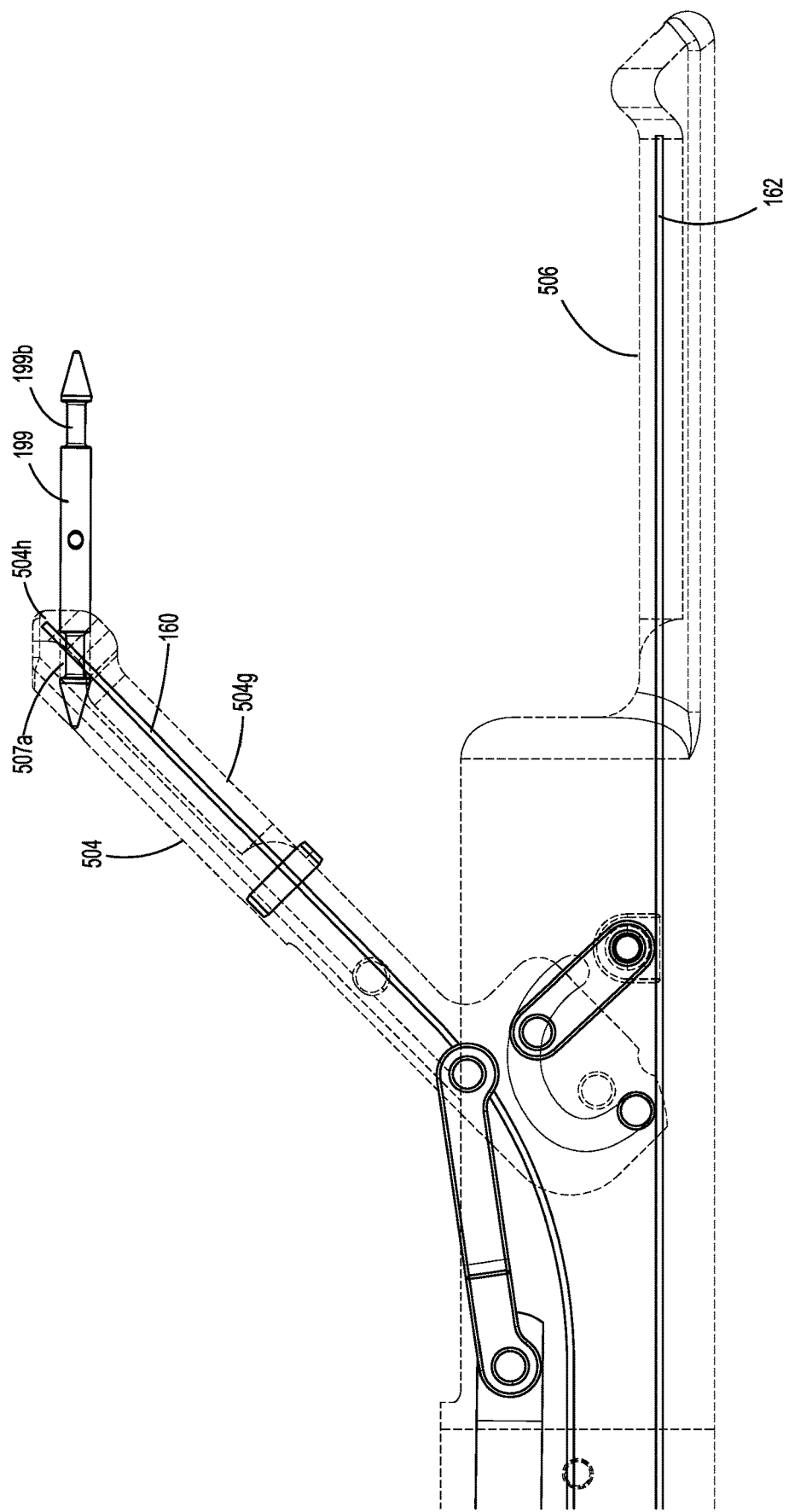
FIGS. 10 and 11 are partial side views of the surgical stitching device of FIG. 1, illustrating use of the tool assembly.
Figure 11:
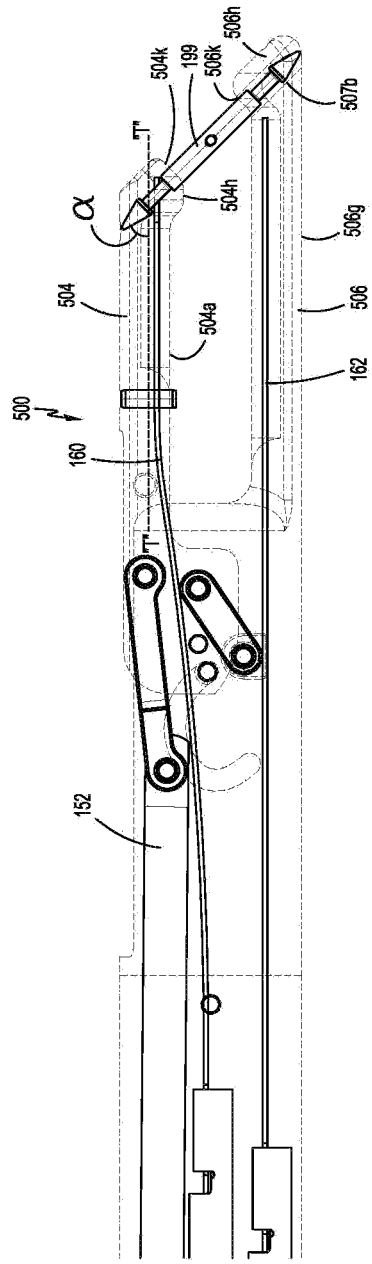

FIGS. 10 and 11 illustrate the suture needle 199 supported on at least one of the first or second jaws 504, 506. In particular, the first jaw 504 includes a first elongate portion 504g and a first receiving portion 504h extending distally from the first elongate portion 504g. The first receiving portion 504h defines a first receiving bore 507a configured to receive a portion of the suture needle 199. The first receiving bore 507a is configured to support the suture needle 199 at, e.g., an acute, angle $\alpha$ with respect to a longitudinal axis "T-T" defined by the first jaw 504. For example, the acute $\alpha$ may be about 45 degrees with respect to the longitudinal axis "T-T". The first receiving portion 504h includes a first planar surface 504k, e.g., in an orthogonal, relation with the suture needle 199. The second jaw 506 includes a second elongate portion 506g and a second receiving portion 506h extending distally from the second elongate portion 506g. The second elongate portion 506g is longer than the first elongate portion 504g. The second receiving portion 506h is distal of the first receiving portion 504h. The second receiving portion 506h defines a second receiving bore 507b configured to receive a portion of the suture needle 199. The second receiving bore 507b is configured to support the suture needle 199 at, e.g., an acute, angle $\beta$ with respect to a longitudinal axis "T-T" defined by the first jaw 504. For example, the acute, angle $\beta$ may be about 45 degrees with respect to the longitudinal axis "T-T." The second receiving portion 506h includes a second planar surface 506k opposing the first planar surface 504k. The first and second planar surfaces 504k and 506k may be substantially parallel to each other. The second planar surface 506k is, e.g., in an orthogonal, relation with the suture needle 199.

In use, the pair of handles 110 is initially squeezed to place the surgical stitching device 10 in the closed configuration, in which, the first and second jaws 504, 506 are approximated (see FIG. 11). At this time, the clinician may position the first and second jaws 504, 506 through an opening in tissue. Thereafter, the pair of handles 110 is released to transition the first and second jaws 504, 506 to the open configuration (see FIG. 10) such that the first and second jaws 504, 506 are spaced apart. At this time, the suture needle 199 may be securely supported on the first jaw 504. While the first and second jaws 504, 506 are in the open configuration, tissue is placed therebetween. The pair of handles 110 is squeezed to transition the first and second jaws 504, 506 to the closed configuration. At this time, the suture needle 199 is received in the second bore 507 of the second jaw 506. Once the suture needle 199 is loaded or at least partially inserted into the second bore 507b, the lever 182 may be pivoted to advance the second blade 162 and retract the first blade 160 such that the notch 162c of the second blade 162 is in registration with the groove 199b of the suture needle 199, and the notch 160b of the first blade 160 disengages from the groove 199a of the suture needle 199. With only the second blade 162 engaged with the suture needle 199, the pair of handles 110 may be released, thereby moving the axial rod 152 proximally to open the first and second jaws 504, 506.

With the first and second jaws 504, 506 in the open position and the suture needle 199 is loaded and held in the second jaw 506, the first and second jaws 504, 506 may be positioned about or over a target tissue and the pair of handles 110 may be actuated to close the first and second jaws 504, 506. As the first and second jaws 504, 506 are approximated, the exposed end of the suture needle 199 is penetrated through the target tissue and the opposed first jaw 504. With the suture needle 199 in the first jaw 504, the lever 182 is once again rotated so that the first and second blades 160, 162 are reversed. In so doing, the suture needle 199 is swapped from the second blade 162 to the first blade 160, and thus, loaded or held in the first jaw 160. The process is repeated, passing the suture needle 199 between the first and second jaws 160, 162 and drawing the suture through the target tissue, thereby suturing the target tissue as needed or desired. In this manner, the suture needle 199 may reliably pass through the typically thick scarred tissue present along, e.g., the edge of midline hernias. The straight suture needle 199 may be suitable to be passed through tissue as needed to close the ventral defect by method of, e.g., extracorporeal running loop suture.

It is envisioned that the surgical stitching device 10 may be configured to connect to a robotic arm of a robotic surgical system to enable manipulation and control thereof. It is also contemplated that the handle assembly 100 may be a powered or electromechanical handle assembly. It is to be understood, therefore, various other changes and modifications may be effected therein by one skilled in the art without departing from the scope or spirit of the disclosure.

While the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. A surgical stitching device comprising:
   an elongate shaft assembly including an axial rod extending through the elongate shaft assembly; and
   a tool assembly coupled with the elongate shaft assembly, the tool assembly including:
      a first jaw and a second jaw, the first jaw operatively coupled with the axial rod of the elongate shaft assembly such that axial displacement of the axial rod transitions the first jaw and the second jaw between an open configuration and a closed configuration;
      a first needle receiving blade slidably disposed in the first jaw and a second needle receiving blade slidably disposed in the second jaw;
      a suture needle supported on the first jaw or the second jaw and defining an acute angle with respect to a longitudinal axis defined by the tool assembly, the suture needle detachably secured to one of the first jaw by the first needle receiving blade or the second jaw by the second needle receiving blade;
      a first bore positioned on the first jaw and defining a first acute angle with respect to a longitudinal axis of the first jaw; and
      a second bore positioned on the second jaw and defining a second acute angle with respect to a longitudinal axis of the second jaw, each of the first bore and the second bore configured to receive a portion of the suture needle.

2. The surgical stitching device according to claim 1, wherein the first jaw includes a first receiving portion and the second jaw includes a second receiving portion, each of the first receiving portion and the second receiving portion configured to support the suture needle.

3. The surgical stitching device according to claim 2, wherein each of the first receiving portion and the second receiving portion includes opposing planar surfaces defining respective acute angles with respect to the longitudinal axis of the tool assembly.

4. The surgical stitching device according to claim 3, wherein the first receiving portion of the first jaw is proximal of the second receiving portion of the second jaw.

5. The surgical stitching device according to claim 1, wherein the suture needle is a straight needle.

6. The surgical stitching device according to claim 1, wherein the acute angle of the suture needle is about 45 degrees.

7. The surgical stitching device according to claim 3, wherein the first receiving portion includes the first bore and the second receiving portion includes the second bore, the first bore and the second bore are orthogonal to the respective planar surfaces.

8. The surgical stitching device according to claim 1, wherein each of the first needle receiving blade and the second needle receiving blade includes respective notches configured to engage the suture needle.

9. The surgical stitching device according to claim 8, wherein the suture needle defines circular grooves on opposite ends of the suture needle.

10. The surgical stitching device according to claim 1, wherein the suture needle extends distally when the suture needle is supported on the first jaw.

11. The surgical stitching device according to claim 1, wherein the suture needle extends proximally when the suture needle is supported on the second jaw.

12. A tool assembly for use with a surgical stitching device, the tool assembly comprising:
- a suture needle having first and second ends;
- first and second jaws transitionable between open and closed configurations, the first jaw including a first elongate portion and a first receiving portion configured to support the first end of the suture needle, the second jaw including a second elongate portion longer than the first elongate portion and a second receiving portion configured to support the second end of the suture needle, the suture needle defining an acute angle with respect to a longitudinal axis defined by the tool assembly when supported on the first or second jaws; and
- first and second needle receiving blades axially movable in reciprocating manner, the first and second needle receiving blades engaging the respective first and second ends of the suture needle to secure the suture needle to the corresponding first or second jaw.

13. The tool assembly according to claim 12, wherein the acute angle is about 45 degrees.

14. The tool assembly according to claim 12, wherein the suture needle is parallel to the longitudinal axis when supported on the first jaw in the open configuration.

15. The tool assembly according to claim 12, wherein the suture needle defines an axis.

16. The tool assembly according to claim 12, wherein the second receiving portion of the second jaw is distal of the first receiving portion of the first jaw.

17. The tool assembly according to claim 12, wherein the first and second receiving portions of the first and second jaws include respective planar surfaces and define respective bores configured to receive a portion of the suture needle, the first and second receiving portions of the first and second jaws extend distally from the respective first and second elongate portions.

18. The tool assembly according to claim 12, wherein the first and second jaws define respective channels configured to slidably receive the first and second blades, and respective bores configured to support the suture needle, each bore is in communication with the corresponding channel.

19. A surgical stitching device comprising:
- an elongate shaft assembly including an axial rod extending through the elongate shaft assembly; and
- a tool assembly coupled with the elongate shaft assembly, the tool assembly including:
  - a first jaw and a second jaw, the first jaw operatively coupled with the axial rod such that axial displacement of the axial rod transitions the first jaw and the second jaw between an open configuration and a closed configuration, the first jaw having a first receiving portion and the second jaw having a second receiving portion, wherein the first receiving portion is proximal of the second receiving portion, and each of the first receiving portion and the second receiving portion includes opposing planar surfaces defining respective acute angles with respect to the longitudinal axis of the tool assembly;
  - a first needle receiving blade slidably disposed in the first jaw and a second needle receiving blade slidably disposed in the second jaw; and
  - a suture needle supported on the first receiving portion of the first jaw or the second receiving portion of the second jaw and defining an acute angle with respect to a longitudinal axis defined by the tool assembly, the suture needle detachably secured to one of the first jaw by the first needle receiving blade or the second jaw by the second needle receiving blade.

20. The surgical stitching device according to claim 19, wherein the suture needle extends distally when the suture needle is supported on the first jaw and the suture needle extends proximally when the suture needle is supported on the second jaw.

* * * * *